United States Patent
Jung et al.

(10) Patent No.: US 10,786,175 B2
(45) Date of Patent: Sep. 29, 2020

(54) SENSORS FOR MEASURING SKIN CONDUCTIVITY AND METHODS FOR MANUFACTURING THE SAME

(71) Applicant: KOREA ELECTRONICS TECHNOLOGY INSTITUTE, Seongnam-si, Gyeonggi-do (KR)

(72) Inventors: Suk Won Jung, Osan-si (KR); Young Chang Jo, Yongin-si (KR); Woo Kyeong Seong, Seongnam-si (KR); Yun Jae Won, Seongnam-si (KR); Hyuck Ki Hong, Yongin-si (KR)

(73) Assignee: Korea Electronics Technology Institute, Gyeonggi-Do (KR)

( * ) Notice: Subject to any disclaimer, the term of this patent is extended or adjusted under 35 U.S.C. 154(b) by 525 days.

(21) Appl. No.: 15/409,405

(22) Filed: Jan. 18, 2017

(65) Prior Publication Data
US 2018/0192911 A1   Jul. 12, 2018

(30) Foreign Application Priority Data
Jan. 10, 2017 (KR) .................. 10-2017-0003653

(51) Int. Cl.
*A61B 5/053* (2006.01)
*A61B 5/00* (2006.01)
*A61B 5/05* (2006.01)

(52) U.S. Cl.
CPC .......... *A61B 5/0531* (2013.01); *A61B 5/6826* (2013.01); *A61B 5/05* (2013.01);
(Continued)

(58) Field of Classification Search
CPC ....... A61B 5/0531; A61B 5/0533; A61B 5/68; A61B 5/6801; A61B 5/6813; A61B 5/6825; A61B 5/6826; A61B 5/6839; A61B 2562/028; A61B 2562/0285; A61B 2562/12; A61B 2562/14; A61B 2562/164
See application file for complete search history.

(56) References Cited

U.S. PATENT DOCUMENTS 6,690,959 B2 * 2/2004 Thompson ........... A61B 5/0006
600/372
6,961,603 B2 * 11/2005 Merilainen ........ A61B 5/04085
600/383

(Continued)

FOREIGN PATENT DOCUMENTS

JP       2008-142541 A      6/2008
KR       20-2006-0005878    5/2006
KR       10-1381487 B1      4/2014

OTHER PUBLICATIONS

Office Action of corresponding Korean Patent Application No. 10-2017-0003653—8 pages (dated Aug. 13, 2018).

*Primary Examiner* — Ronald Hupczey, Jr.
*Assistant Examiner* — Bradford C. Blaise
(74) *Attorney, Agent, or Firm* — Knobbe, Martens, Olson & Bear LLP

(57) ABSTRACT

Disclosed is a sensor for measuring skin conductivity and a method of manufacturing the same, wherein the sensor includes: a base board made of a flexible material; an electrode provided on a surface of the base board, and transmitting an electrical signal; and an uneven structure provided on the electrode, and configured to increase an electrical contact area with skin via sweat secreted onto a surface of skin.

7 Claims, 13 Drawing Sheets

(52) U.S. Cl.
CPC .............. *A61B 5/0533* (2013.01); *A61B 5/68* (2013.01); *A61B 5/6801* (2013.01); *A61B 5/6839* (2013.01); *A61B 2562/12* (2013.01); *A61B 2562/14* (2013.01); *A61B 2562/164* (2013.01)

(56) References Cited

U.S. PATENT DOCUMENTS

| | | | | |
|---|---|---|---|---|
| 7,359,744 | B2* | 4/2008 | Lee | A61B 5/04085 600/391 |
| 8,644,904 | B2* | 2/2014 | Chang | C25D 5/56 600/372 |
| 8,700,122 | B2* | 4/2014 | Cordero | A61B 5/0478 600/382 |
| 8,774,890 | B2* | 7/2014 | Ready | A61N 1/05 600/377 |
| 9,414,758 | B1* | 8/2016 | Brockway | A61B 5/6804 |
| 9,504,396 | B2* | 11/2016 | Korkala | A61B 5/6804 |
| 9,700,221 | B2* | 7/2017 | Rajaraman | A61B 5/04001 |
| 2004/0122336 | A1* | 6/2004 | Jang | A61B 5/0531 600/547 |
| 2008/0215128 | A1* | 9/2008 | Rainey | A61N 1/0452 607/152 |
| 2014/0020936 | A1* | 1/2014 | Kim | H05K 1/02 174/255 |
| 2014/0135608 | A1* | 5/2014 | Gazzoni | A61N 1/04 600/395 |
| 2015/0238100 | A1* | 8/2015 | Lin | A61B 5/0478 600/393 |
| 2016/0174859 | A1* | 6/2016 | Oudenhoven | A61B 5/04 600/383 |
| 2016/0270680 | A1* | 9/2016 | Kim | A61B 5/04001 |
| 2017/0209079 | A1* | 7/2017 | Kinser | A61B 5/1486 |
| 2017/0367614 | A1* | 12/2017 | Zuckerman-Stark | A61B 5/6831 |

\* cited by examiner

SENSORS FOR MEASURING SKIN CONDUCTIVITY AND METHODS FOR MANUFACTURING THE SAME

CROSS REFERENCE TO RELATED APPLICATION

The present application claims priority to Korean Patent Application No. 10-2017-0003653, filed Jan. 10, 2017, the entire contents of which is incorporated herein for all purposes by this reference.

BACKGROUND OF THE INVENTION

Field of the Invention

The present invention relates generally to a sensor for measuring skin conductivity and a method of manufacturing the same.

Description of the Related Art

Medical research has shown that stress has a negative effect on persons. Examples of such negative effects include reduced concentration, negative emotions, and increased aggression. Based on this research, it is important to be able to objectively and accurately measure stress levels in order to determine how much stress a person is currently experiencing and provide feedback that recommends appropriate measures.

When a person is stressed, the sympathetic nervous system becomes excited, and the sweat glands present in skin are activated in accordance with excitation of the sympathetic nervous system. The electrical characteristics of skin are changed in accordance with activity of the sweat glands present in skin. These changes are called electrodermal activity (EDA), which can be measured to determine a person's stress levels.

The foregoing is intended merely to aid in the understanding of the background of the present invention, and is not intended to mean that the present invention falls within the purview of the related art that is already known to those skilled in the art.

DOCUMENTS OF RELATED ART (Patent Document 1) Korean Utility Model Registration No. 20-0416389 (issued May 8, 2006)

SUMMARY OF THE INVENTION

Accordingly, the present invention has been made keeping in mind the above problems occurring in the related art, and the present invention is intended to propose a sensor for measuring skin conductivity and a method of manufacturing the same, wherein an uneven structure is provided on an electrode, which is provided on a base board made of a flexible material to come into contact with skin, and is configured to increase an electrical contact area with skin via sweat secreted onto a surface of skin.

Further, the present invention is intended to propose a sensor for measuring skin conductivity and a method of manufacturing the same, wherein the uneven structure is provided on a first electrode and a second electrode, and also on the base board at locations between the first and second electrodes.

Further, the present invention is intended to propose a sensor for measuring skin conductivity and a method of manufacturing the same, wherein a plurality of through holes is formed through the base board, the electrode, and the uneven structure in a direction perpendicular to a surface of the base board.

In order to achieve the above object, according to one aspect of the present invention, there is provided a sensor for measuring skin conductivity, the sensor including: the base board made of a flexible material; the electrode provided on a surface of the base board, and transmitting an electric signal; and the uneven structure provided on the electrode, and configured to increase an electrical contact area with skin via sweat secreted onto the surface of skin.

Further, the electrode may include: the first electrode; and the second electrode electrically insulated from the first electrode, wherein each of the first and second electrodes includes a measurement area in contact with skin and a connection area to which an external circuit is connected.

Further, the uneven structure may include a Pt-black layer structure provided on the electrode and configured to have a porous nanostructure formed of platinum particles.

Further, the uneven structure may include a plurality of pillar structures provided on the electrode.

Further, the uneven structure may be provided on the measurement areas of the first and second electrodes, and may be provided on the base board at locations between the measurement areas of the first and second electrodes.

Further, the uneven structure may be configured to have protrusions, with gaps defined between the protrusions, so that the sweat secreted onto the surface of skin permeates between the protrusions by a capillary phenomenon.

Further, the uneven structure may be configured to have protrusions that have heights determined such that when the sweat secreted onto the surface of skin permeates between the protrusions, the sweat is free from reaching the electrode.

Further, the uneven structure may be configured to have protrusions that have heights determined such that when the sweat secreted onto the surface of skin permeates between the protrusions, the sweat reaches the electrode.

Further, each of the first and second electrodes includes a plurality of first branches that are configured such that the first branches of the first electrode and the first branches of the second electrode are formed in a comb pattern.

Further, the sensor may further include a plurality of through holes formed through the base board, the electrode, and the uneven structure in the direction perpendicular to the surface of the base board.

In order to achieve the above object, according to another aspect of the present invention, there is a provided a method of manufacturing a sensor for measuring skin conductivity, the method including: preparing a base board on a carrier board; forming an electrode on the base board by forming and patterning a conductive material; forming an uneven structure on the electrode such that an electrical contact area with skin is increased by sweat secreted onto a surface of skin; and removing the carrier board.

Further, the method may further include forming a plurality of through holes through the base board, the electrode, and the uneven structure in a direction perpendicular to a surface of the base board after the forming of the uneven structure.

Further, in the forming of the uneven structure, the uneven structure is formed on both the electrode and the base board.

The above and other objects, features and advantages of the present invention will be more clearly understood from the following detailed description when taken in conjunction with the accompanying drawings.

All terms or words used in the specification and claims have the same meaning as commonly understood by one of ordinary skill in the art to which inventive concepts belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

According to the sensor for measuring skin conductivity with the above-described configuration, the uneven structure is provided on the electrode provided on the base board made of the flexible material to come into close contact with skin, whereby it is possible to measure that the skin-electrode contact resistance Rct is drastically reduced as the electrical contact area between skin and the electrode is enlarged by the sweat secreted onto the surface of skin. Thus, electrodermal activity can be efficiently measured.

In addition, the electrode includes the first and second electrodes, the uneven structure is provided on the first and second electrodes, and also on the base board at the locations between the first and second electrodes, whereby the electrical signal passing between the first and second electrodes can be transmitted through not only the inside of skin but also through the sweat and the uneven structure. Thus, electrodermal activity can be efficiently measured.

Moreover, the plurality of through holes is formed through the base board, the electrode, and the uneven structure in the direction perpendicular to the surface of the base board, whereby the sweat secreted onto the surface of skin can be rapidly evaporated by air flowing through the through holes. Thus, in measuring skin electrical activity, it is possible to eliminate measurement errors that occur when the sweat is accumulated on the uneven structure.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Figure 1:
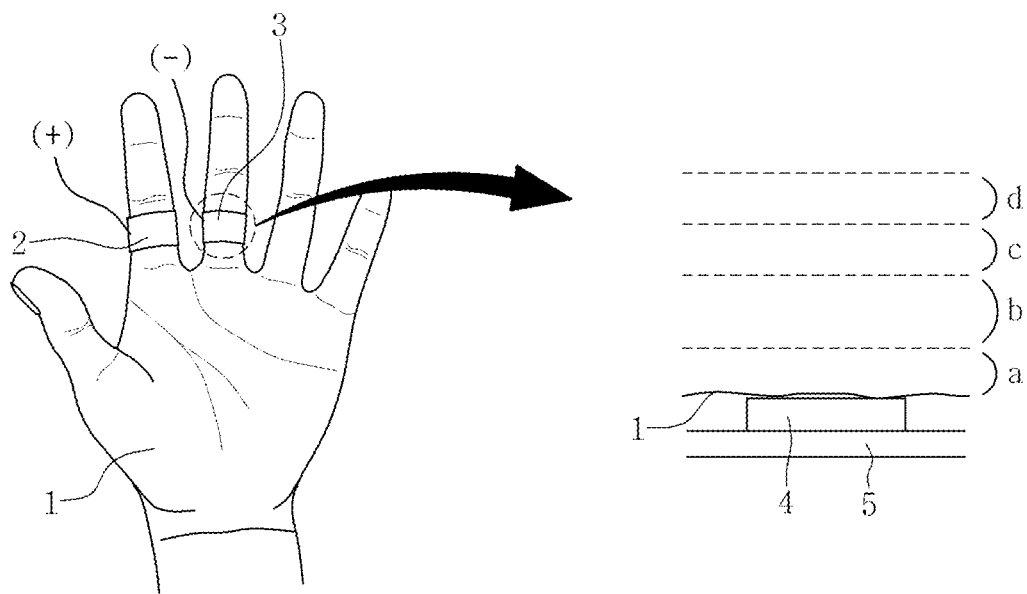
FIG. 1 is a view showing a conventional sensor for measuring skin conductivity.

The above and other objects, features and advantages of the present invention will be more clearly understood from the following detailed description taken in conjunction with the accompanying drawings. Reference now should be made to the drawings, in which the same reference numerals are used throughout the different drawings to designate the same or similar components. Further, it will be understood that, although the terms "one side", "the other side", "first", "second", etc. may be used herein to describe various elements, these elements should not be limited by these terms. Further, in the following description, when it is determined that the detailed description of the known art related to the present invention might obscure the gist of the present invention, the detailed description thereof will be omitted.

Hereinbelow, exemplary embodiments of the present invention will be described in detail with reference to the accompanying drawings. Throughout the drawings, the same reference numerals will refer to the same or like parts.

Figure 2:
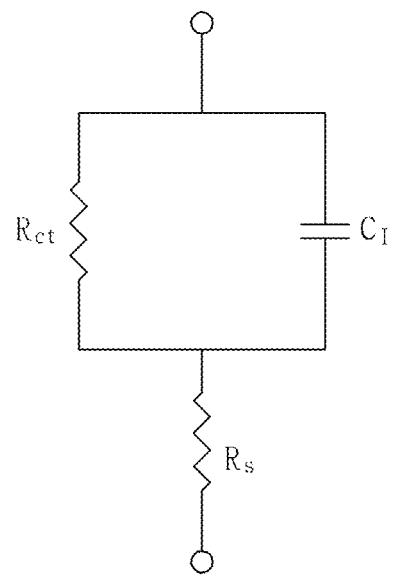
FIG. 2 is a view showing impedance model between skin and an electrode of the sensor for measuring skin conductivity.

FIG. 1 is a view showing a conventional sensor for measuring skin conductivity, and FIG. 2 is a view showing impedance model between skin and an electrode of the sensor for measuring skin conductivity.

As shown in FIG. 1, a conventional method of measuring skin conductivity is a method in which a pair of sensors 2 and 3 for measuring skin conductivity are worn on fingers of a user, and an electrical signal having a positive (+) polarity and an electrical signal having a negative (−) polarity are applied to the sensors 2 and 3 respectively. The Electrical signal is transmitted from an electrode 4 of the sensor 2 to the sensor 3 through skin 1, and is affected by a change in electrical characteristics of skin. Generally, when a person is stressed, the sympathetic nervous system is excited and then sweat glands present in skin are activated in response to excitation of the sympathetic nervous system, and thus electrical characteristics of skin are changed. The change in electrical characteristics of skin due to stress is represented by a change in the electrical signal, and the change in the electrical signal is measured by the electrode 4 coupled to the sensor body 5, thereby measuring a user's stress levels.

With reference to both an enlarged view of FIG. 1 and FIG. 2, the human skin 1 is composed of a skin layer a, a dermal layer b, a subcutaneous fat layer c, and a muscle layer d. Resistance Rs inside skin, which affects the electrical signal passing through an inside of skin 1, can be modeled as a parallel connection of resistance Ra of skin layer a, resistance Rb of the dermal layer b, resistance Rc of the subcutaneous fat layer c, and resistance Rd of the muscle layer d. Impedance between skin 1 and the electrode 4 of the sensor for measuring skin conductivity can be modeled as a parallel connection of skin-electrode contact resistance Rct and skin-electrode capacitance $C_I$.

In this model, a total of skin-electrode impedance Z is as shown in Equation 1 below, and skin conductivity G is as shown in Equation 2. Since skin conductivity G is measured by using a DC signal (frequency is 0, that is, w=0), measured skin conductivity G can be summarized as shown in Equation 3.

$$Z = \frac{1}{\frac{1}{R_{ct}} + j\omega C_I} + R_S \qquad \text{Equation 1}$$

$$G = \frac{1}{Z} = \frac{1}{\frac{1}{\frac{1}{R_{ct}} + j\omega C_I} + R_S} \qquad \text{Equation 2}$$

$$G(\omega = 0) = \frac{1}{R_{ct} + R_S} \qquad \text{Equation 3}$$

Figure 3A:
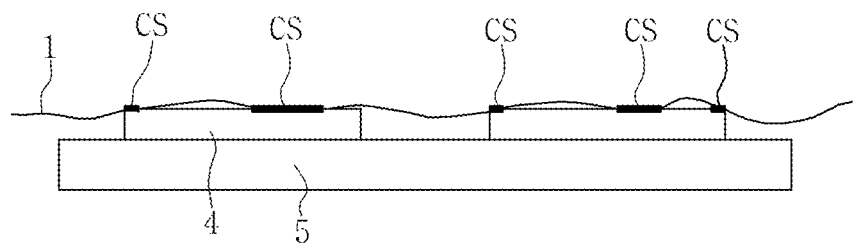
FIGS. 3A and 3B are views showing a principle of stress measurement of the conventional sensor for measuring skin conductivity.
Figure 3B:
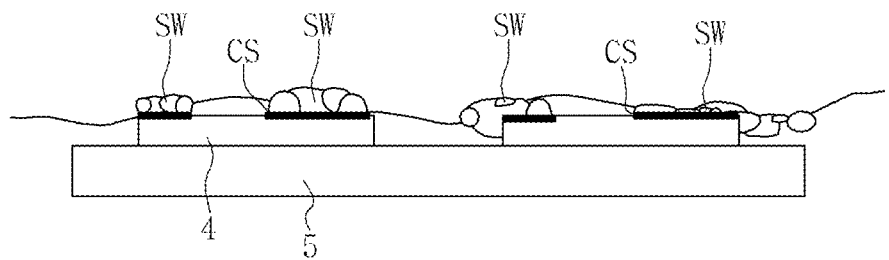

FIGS. 3A and 3B are views showing a principle of stress measurement of the conventional sensor for measuring skin conductivity. As shown in FIG. 3A, a surface of the electrode 4 of the conventional sensor for measuring skin conductivity and a surface of skin 1 partially come into contact with each other due to curves of the surface of skin 1. Accordingly, an area of a skin-electrode contact surface CS is smaller than a surface area of the electrode 4, and skin-electrode contact resistance Rct is high.

When the person is stressed and the sweat glands are activated by excitation of the sympathetic nervous system, the sweat SW is secreted onto the surface of skin 1. The sweat SW includes an electrolyte and has electrical conductivity, and the sweat SW is filled between skin 1 and the electrode 4, thereby enlarging the area of skin-electrode contact surface CS. Since resistance is inversely proportional to an area, skin-electrode contact resistance Rct is reduced as the area of skin-electrode contact surface CS is enlarged. Accordingly, electrodermal activity is measured by measuring a reduction in contact resistance Rct.

As shown in FIG. 1, the conventional sensor for measuring skin conductivity has to be worn on the palm or fingers of a user's hand, in which the sweat glands are more active due to excitation of the sympathetic nervous system. As a result, the conventional sensor is inconvenient to constantly wear to measure a change in stress levels in daily life. In addition, there is no significant difference in area between skin-electrode contact surface CS in a state where no sweat SW is secreted on to the surface of skin 1 (see FIG. 3A) and skin-electrode contact surface CS in a state where the sweat SW is secreted onto the surface of skin 1 (see FIG. 3B). Thus, there is a problem in that it is difficult to sensitively measure electrodermal activity because the area of the skin-electrode contact surface CS according to the stress state is not significantly changed.

If the sensor for measuring skin conductivity is attached to a body part (where activity of the sweat glands is less active compared to the palm of the hand) that does not cause discomfort in daily life, it is difficult to efficiently measure stress due to such low sensitivity.

Figure 4:
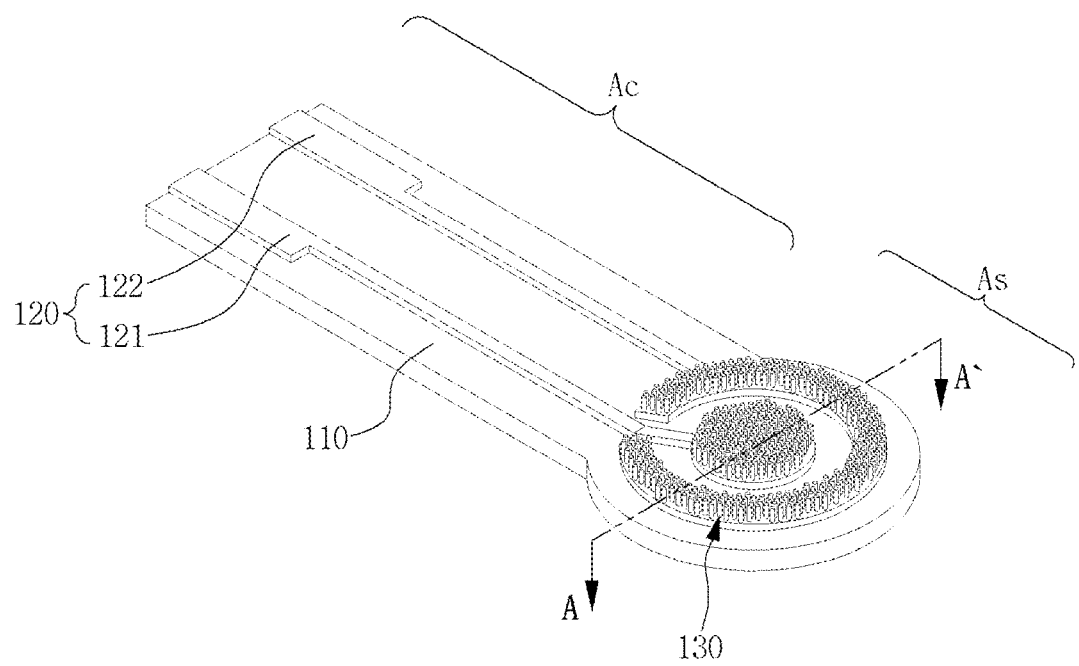
FIG. 4 is a perspective view showing a sensor for measuring skin conductivity according to an embodiment of the present invention.
Figure 5:
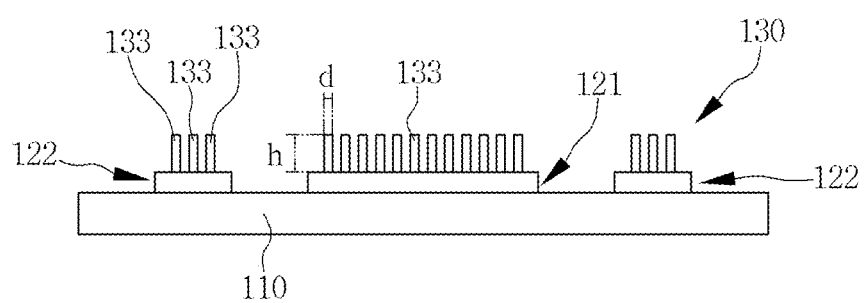
FIG. 5 is a cross-sectional view taken along line A-A' of FIG. 4.
Figure 6:
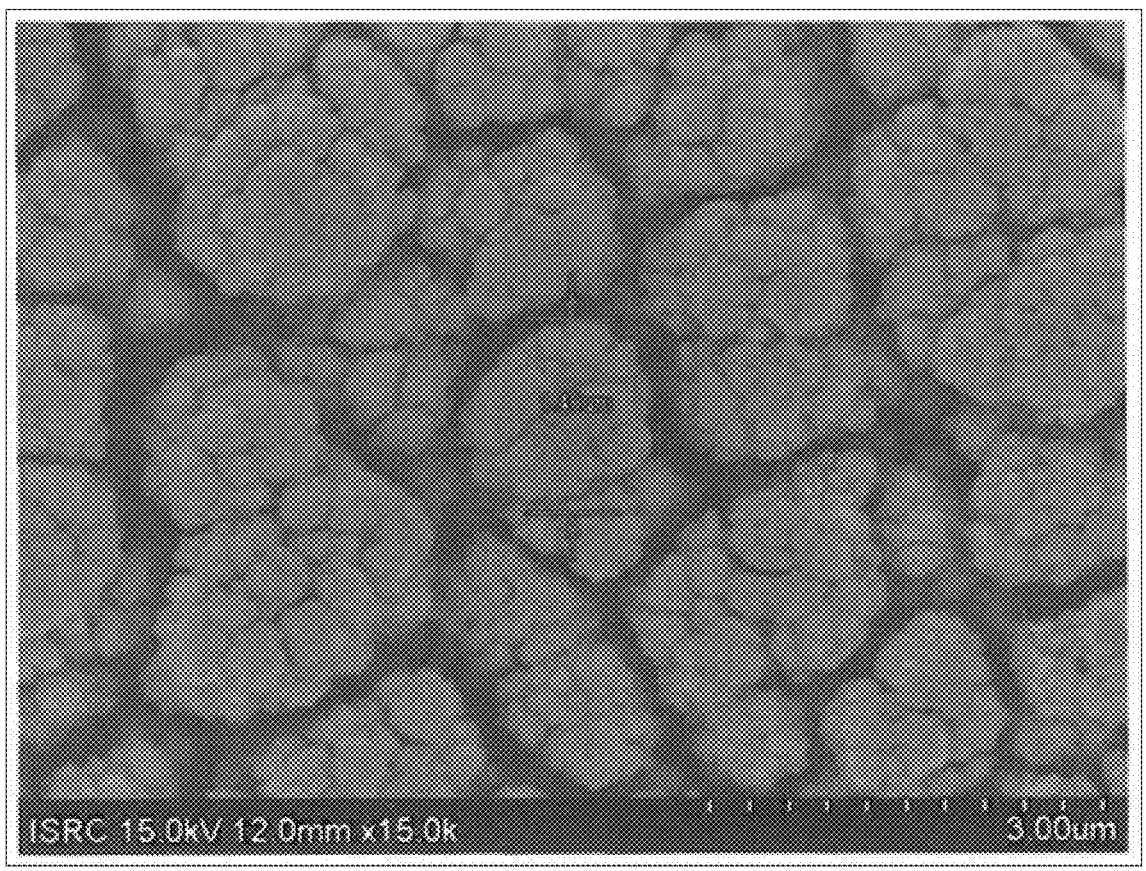
FIG. 6 is a view showing a Pt-black layer according to the embodiment of the present invention.
Figure 7A:
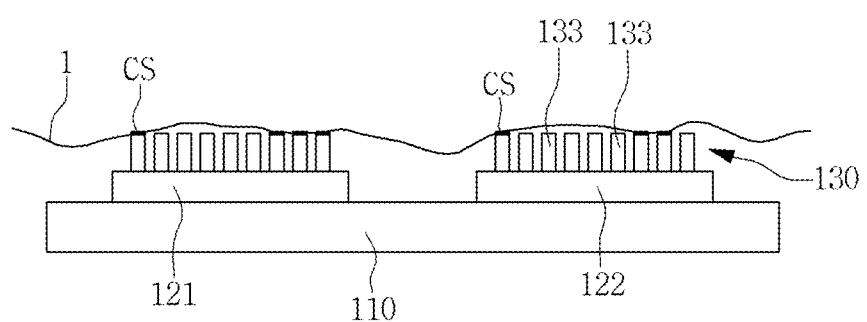
FIGS. 7A and 7B are views showing a principle of stress measurement of the sensor for measuring skin conductivity according to the embodiment of the present invention.
Figure 7B:
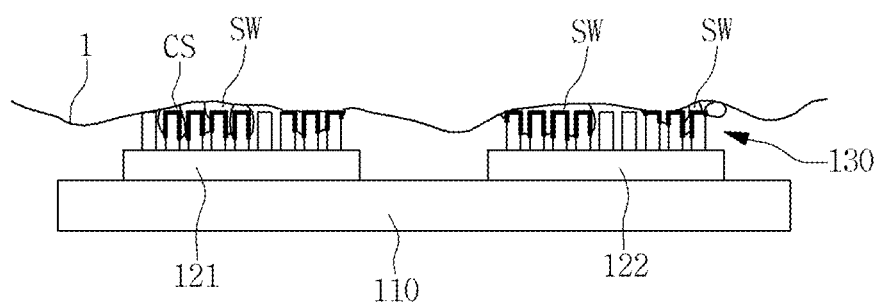

FIG. 4 is a perspective view showing a sensor for measuring skin conductivity according to an embodiment of the present invention, FIG. 5 is a cross-sectional view taken along line A-A' of FIG. 4, FIG. 6 is a view showing a PT-black layer according to the embodiment of the present invention, and FIGS. 7A and 7B are views showing a principle of stress measurement of the sensor for measuring skin conductivity according to the embodiment of the present invention.

In an effort to solve the above problems of the conventional sensor for measuring skin conductivity, the sensor for measuring skin conductivity according to the embodiment of the present invention includes a base board 110 made of a flexible material, an electrode 120 provided on a surface of the base board 110 and transmitting an electrical signal, and an uneven structure 130 provided on the electrode 120 and configured to increase an electrical contact area with skin 1 via sweat SW secreted onto the surface of skin 1.

The base board 110 is made of the flexible material, such that the sensor for measuring skin conductivity can be brought into close contact with skin 1. The base board 110 may be made of a Flexible PCB (FPCB) or the like. The base board 110 supports the electrode 120 provided on the surface of the base board 110, and serves as a body of the sensor for measuring skin conductivity.

As shown in FIG. 1, the electrode 120 includes a first electrode 121, and a second electrode 122 electrically insulated from the first electrode 121, wherein each of the first and second electrodes 121 and 122 includes a measurement area As in contact with skin 1 and a connection area Ac to which an external circuit is connected. The sensor for measuring skin conductivity is provided with the first electrode 121 and the second electrode 122 at the same time, such that skin conductivity can be measured at one point and an area of the sensor can be reduced unlike the conventional sensor for measuring skin conductivity shown in FIG. 1.

The first and second electrodes 121 and 122 are made of a conductive material, and the electrical signal is input thereto. The measurement area As is a region where skin 1 comes into contact therewith, thereby measuring electrodermal activity, and the first and second electrodes 121 and 122 are provided with the uneven structure 130. The connection area Ac is a region where the external circuit is connected thereto such that the electrical signal is input from the external circuit. For example, the positive (+) polarity may be connected to the connection region Ac of the first electrode 121, and the negative (−) polarity may be connected to the connection region Ac of the second electrode 122.

The uneven structure 130 is provided on the measurement area As of the electrode 120. For example, as shown in FIGS. 4 and 5, the uneven structure 130 may comprise a plurality of pillar structures provided on the electrode 120. The pillar structures are protrusions 133 provided to be spaced apart from each other at regular intervals, wherein each of the protrusions 133 may have a diameter d of 10 μm and a height h of 1 μm, or may have a diameter d of 5 μm and a height h of 5 μm.

As shown in FIG. 6, the uneven structure 130 may include a Pt-black layer structure provided on the electrode 120 and configured to have a porous nanostructure formed of platinum particles. The Pt-black layer is formed by electroplating platinum on the electrode 120 to have an irregular porous structure. Since a surface area of the Pt-black layer is much larger than that of the electrode 120 having a flat surface, the sweat SW secreted onto the surface of skin 1 permeates into the Pt-black layer, and thus the area of skin-electrode contact surface CS is significantly changed.

The uneven structure 130 may include structures having a conductive property, having the protrusions 133, and in which a contact area is enlarged by the sweat SW secreted onto the surface of skin 1, without being limited to the pillar structures or the Pt-black layer.

The uneven structure 130, namely the pillar structures and the Pt-black layer, has a structure in which when the sensor for measuring skin conductivity is brought into contact with skin 1, upper ends of the protrusions 133 of the uneven structure 130 come into contact with the surface of skin 1, whereas side surfaces of the protrusions 133 or a surface of the electrode 120 between the protrusions 133 does not come into contact with the surface of skin 1. Thus, skin-electrode contact resistance Rct measured in the state where no sweat SW is secreted onto the surface of skin 1 is higher than that of the conventional sensor for measuring skin conductivity, in which there is no uneven structure 130 and the electrode 120 directly comes into contact with the surface of skin 1.

In other words, because the area of skin-electrode contact surface CS shown in FIG. 7A is smaller than that of skin-electrode contact surface CS shown in FIG. 3A, skin-electrode contact resistance Rct of the sensor for measuring skin conductivity (FIG. 7A) according to the embodiment of the present invention is higher than that of the conventional sensor for measuring skin conductivity (FIG. 3A).

In addition, skin-electrode contact resistance Rct measured in the state where sweat SW is secreted onto skin 1 is lower than that of the conventional sensor for measuring skin conductivity, in which there is no uneven structure 130 and the electrode 120 directly comes into contact with the surface of skin 1.

In other words, because the area of skin-electrode contact surface CS shown in FIG. 7B is larger than that of skin-electrode contact surface CS shown in FIG. 3B, skin-electrode contact resistance Rct of the sensor for measuring skin conductivity (FIG. 7B) according to the embodiment of the present invention is lower than that of the conventional sensor for measuring skin conductivity (FIG. 3B).

Thus, the uneven structure 130 increases difference between skin-electrode contact resistance Rct measured in the unstressed state (state in which no sweat SW is secreted onto the surface of skin 1) and skin-electrode contact resistance Rct measured in the stressed state (state in which the sweat SW is secreted onto the surface of skin 1).

Accordingly, the sensor for measuring skin conductivity according to the embodiment of the present invention has a larger difference in contact resistance Rct than the conventional sensor for measuring skin conductivity, and thereby has high sensitivity. Thus, even if the sensor is attached to an inner surface of the wrist or the chest of a user, in addition to the palm where activity of the sweat glands is active, it is possible to efficiently measure user's stress levels.

Figure 8A:
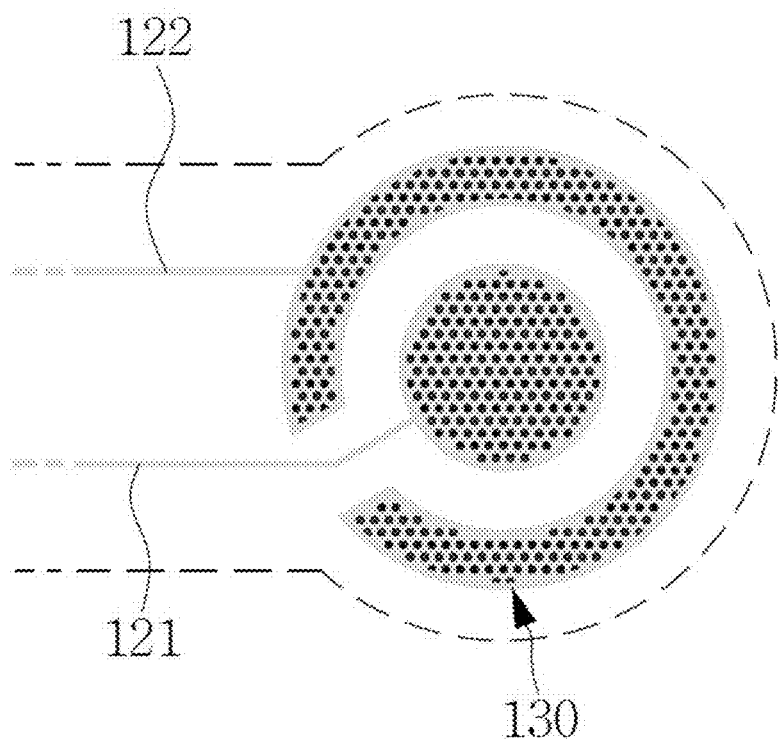
FIGS. 8A, 8B, and 8C are views showing various types of an electrode of FIG. 4.
Figure 8B:
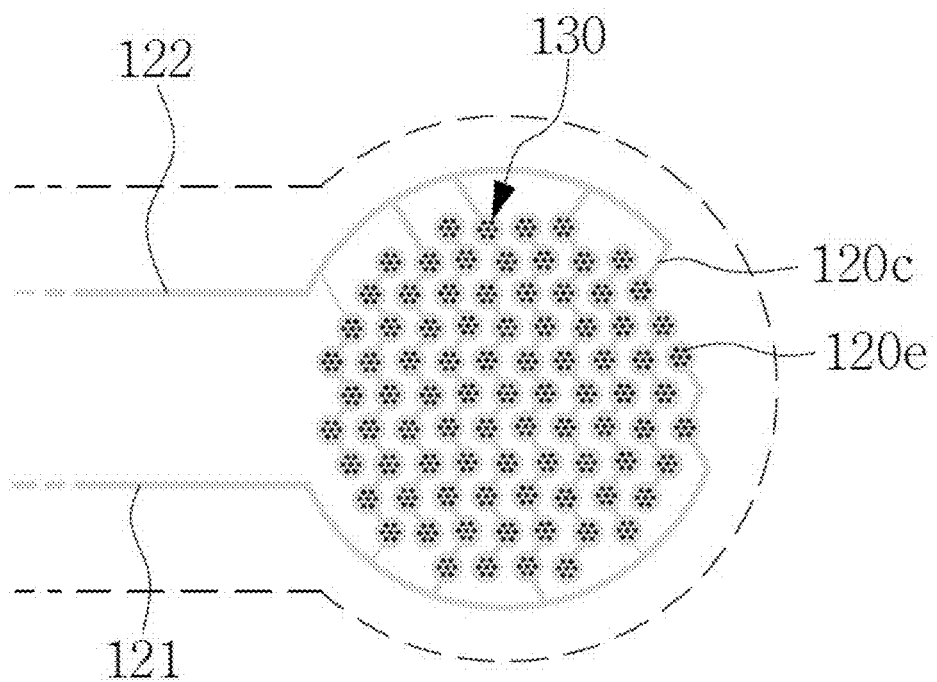
Figure 8C:
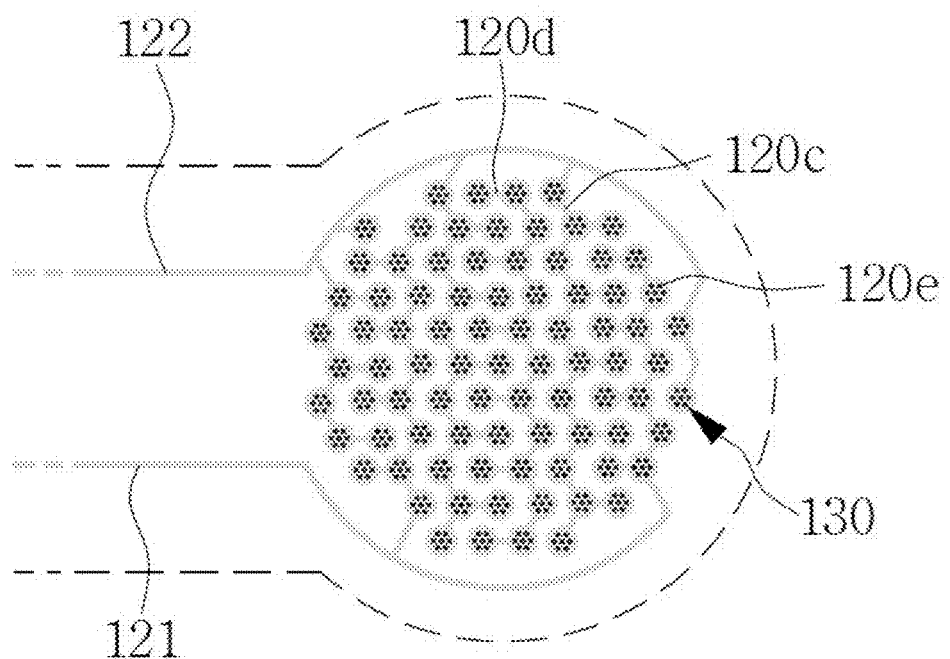

FIGS. 8A, 8B, and 8C are views showing various types of the electrode 120 of FIG. 4. As shown in FIG. 8A, the measurement area As of the first electrode 121 is formed in a circular shape, and the measurement area As of the second electrode 122 is spaced apart from a circular part of the first electrode 121 by a predetermined distance, thereby being formed in a ring shape to surround the circular part.

Alternatively, as shown in FIG. 8B, the measurement area As of the first electrode 121 and the measurement area As of the second electrode 122 may be formed in a comb shape. A first branch 120c of the first electrode 121 is formed in a direction of the second electrode 122, and a first branch 120c of the second electrode 122 is formed in a direction of first electrode 121, thereby forming the comb shape. In other words, each of the first and second electrodes 121 and 122 includes a plurality of first branches 120c, such that the first branches 120c of the first and second electrodes 121 and 122 are formed in a comb pattern. The first branches 120c may be formed in a zigzag shape, measurement points 120e having widths larger than that of the first branches 120c are provided at the first branches 120c at regular intervals, and the uneven structure 130 is provided on the measurement points 120e.

Further alternatively, as shown in FIG. 8C, the measurement area As of the first electrode 121 and the measurement area As of the second electrode 122 are formed in the comb shape, wherein each of the first branches 120c includes a plurality of second branches 120d, such that the second branches 120d of the first and second electrodes 121 and 122 are formed in the comb pattern. The measurement points 120e are provided at the first branches 120c and the second branches 120d, and the uneven structure 130 is provided on the measurement points 120e.

When compared to the electrode 120 shown in FIG. 8A, the electrode 120 shown in FIG. 8B or 8C has a structure in which a distance between the first and second electrodes 121 and 122 is small, and the first and second electrodes 121 and 122 are uniformly distributed due to the comb shape. Thus, electrodermal activity can be efficiently measured.

Figure 9A:
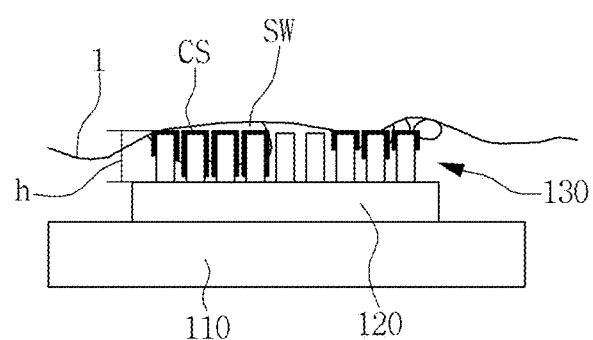
FIGS. 9A and 9B are views showing a difference in accordance with a height of an uneven structure of FIG. 4.
Figure 9B:
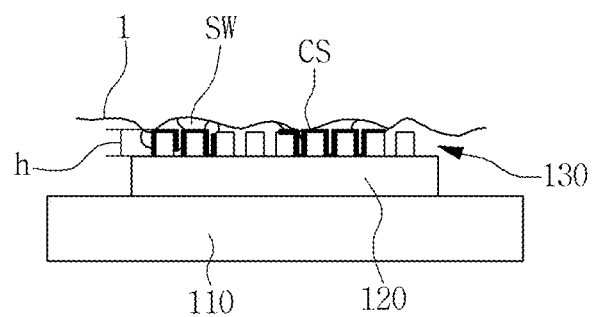

FIGS. 9A and 9B are views showing a difference in accordance with a height of the uneven structure 130 of FIG. 4. As shown in FIG. 9A, the protrusions 133 of the uneven structure 130 may have heights h determined such that even if the sweat SW secreted onto the surface of skin 1 permeates between the protrusions 133, the sweat SW is free from reaching the electrode 120. When the heights h of the protrusions 133 are sufficiently high, the sweat SW secreted onto the surface of skin 1 may come into contact with the side surfaces of the protrusions 133 and may not reach the surface of the electrode 120. Here, the side surfaces of the protrusions 133 are brought into electrical contact with the surface of skin 1 by the sweat SW, such that the area of skin-electrode contact surface CS is enlarged and skin-electrode contact resistance Rct is drastically reduced. Thus, sensitivity of the sensor for measuring skin conductivity is increased.

Further, as shown in FIG. 9B, the protrusions 133 of the uneven structure 130 may have heights h determined such that when the sweat SW secreted onto the surface of skin 1 permeates between the protrusions 133, the sweat SW reaches on the electrode 120. When the heights h of the protrusions 133 are sufficiently low, the sweat SW secreted onto the surface of skin 1 comes into contact with both the side surfaces of the protrusions 133 and the surface of the electrode 120. Accordingly, the area of skin-electrode contact surface CS is enlarged and skin-electrode contact resistance Rct is drastically reduced. Thus, sensitivity of the sensor for measuring skin conductivity is increased.

Moreover, the protrusions 133 of the uneven structure 130 may have gaps therebetween, so that the sweat SW secreted onto the surface of skin 1 permeates between the protrusions 133 by a capillary phenomenon. In this case, even when a small amount of sweat SW is secreted onto the surface of skin 1, the sweat SW can permeate between the protrusions 133 by capillary phenomenon. Accordingly, the area of skin-electrode contact surface CS is enlarged and skin-electrode contact resistance Rct is drastically reduced. Thus, sensitivity of the sensor for measuring skin conductivity is increased.

Figure 10A:
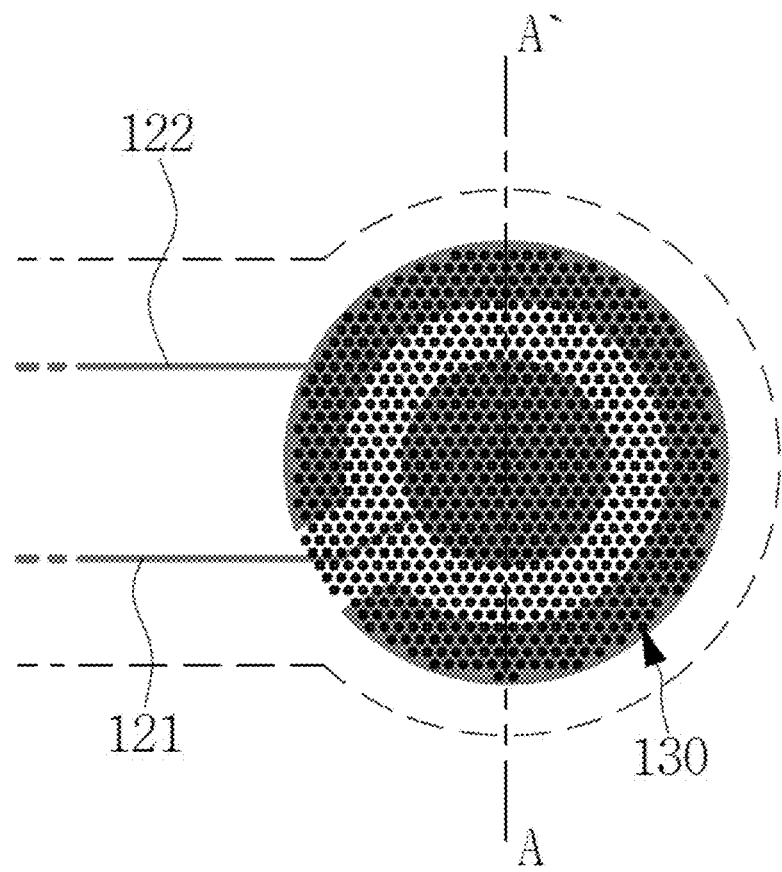
FIGS. 10A, 10B, and 10C are views showing the uneven structure provided at an entire measurement area of FIG. 4.
Figure 10B:
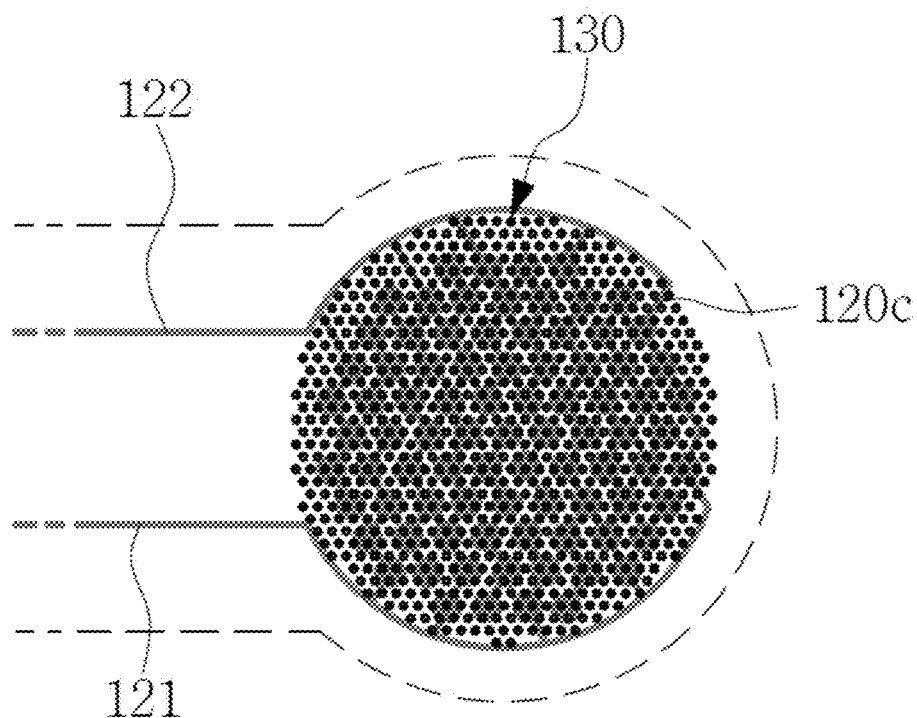
Figure 10C:
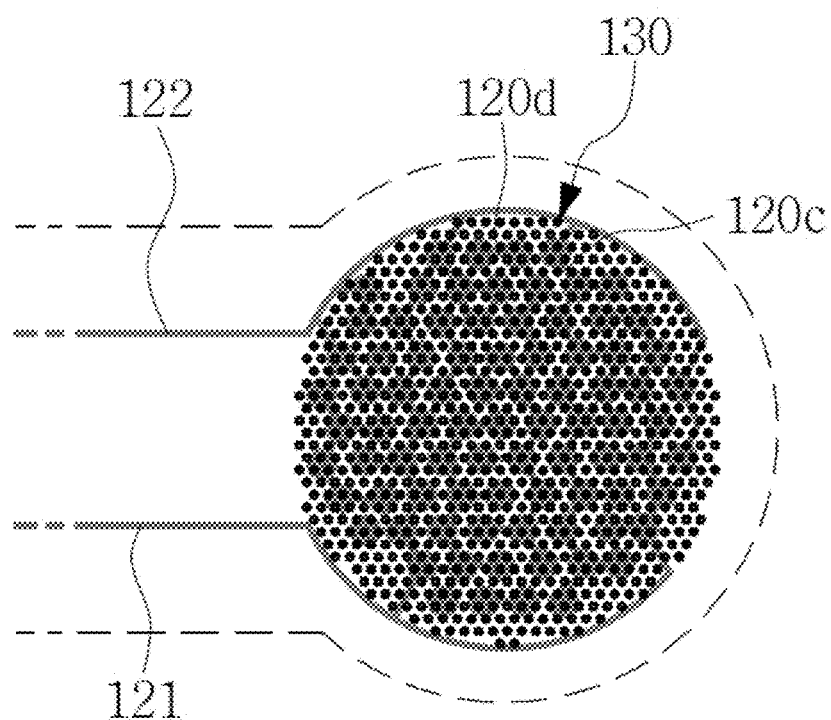
Figure 11A:
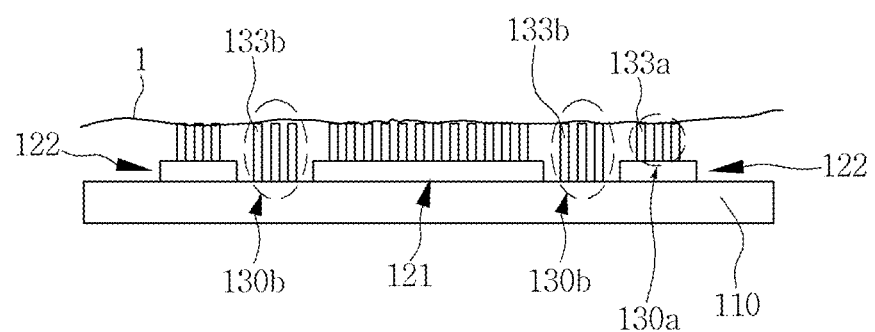
FIGS. 11A and 11B are cross-sectional views taken along line A-A' of FIG. 10A.
Figure 11B:
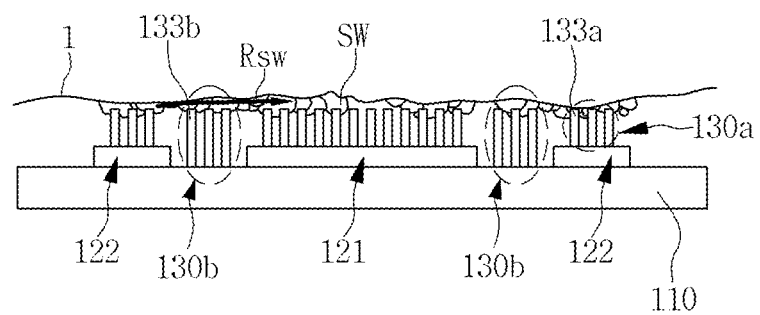

FIGS. 10A, 10B, and 10C are views showing the uneven structure 130 provided at the entire measurement area As of FIG. 4, and FIGS. 11A and 11B are cross-sectional views taken along line A-A' of FIG. 10A.

As shown in FIGS. 10A to 11B, the uneven structure 130 is provided at the measurement areas As of the first and second electrodes 121 and 122, and also on the base board 110 at locations between the measurement areas As of the first and second electrodes 121 and 122. In other words, the protrusions 133 are further provided between the first and second electrodes 121 and 122.

As shown in FIG. 11A, protrusions 133b of an uneven structure 130b are provided on the base board 110 at locations between the first and second electrodes 121 and 122, such that upper ends of the protrusions 133b are aligned with upper ends of protrusions 133a of an uneven structure 130a provided on the electrode 120. As shown in FIG. 11B, when the sweat SW is secreted onto the surface of skin 1, the sweat SW permeates between the protrusions 133b provided on the base board 110, thereby forming a path Rsw by the protrusions 133b provided on the base board 110 and the sweat SW. This path Rsw connects the first electrode 121 and the second electrode 122 to each other, whereby the electrical signal can be transmitted along the surface of skin 1 without passing through the inside of skin 1.

Moreover, even if the first and second electrodes 121 and 122 are not connected to each other by the protrusions 133b provided on the base board 110 and the sweat SW, the amount of the electrical signal passing through the inside of skin 1 can be minimized by the path Rsw formed by the protrusions 133b provided on the base board 110 and the sweat SW.

Thus, as the sweat SW permeates between the protrusions 133b provided on the base board 110 at locations between the first and second electrodes 121 and 122, skin-to-electrode contact resistance Rct is drastically reduced. Thus, sensitivity of the sensor for measuring skin conductivity is increased.

Figure 12:
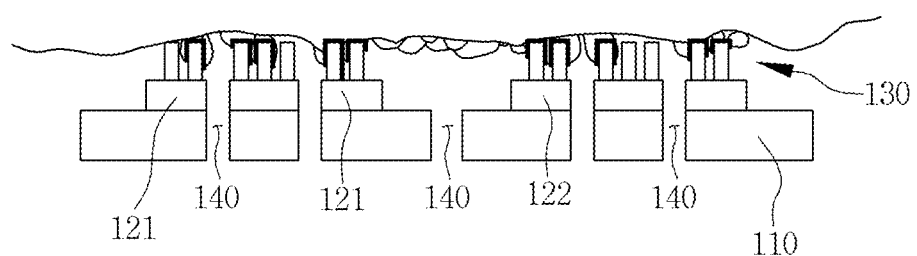
FIG. 12 is a cross-sectional view showing a plurality of through holes formed at the sensor for measuring skin conductivity shown in FIG. 4.

FIG. 12 is a cross-sectional view showing a plurality of through holes 140 formed at the sensor for measuring skin conductivity shown in FIG. 4. As shown in FIG. 12, the through holes 140 are formed through the base board 110, the electrode 120, and the uneven structure 130 in a direction perpendicular to the surface of the base board 110. Accordingly, even when the sensor for measuring skin conductivity covers the surface of skin 1, air can flow through the through holes 140. Thus, the sweat SW permeating between the surface of skin 1 and the protrusions 133 can be evaporated.

If the sweat SW remains between the protrusions 133 after the sweat SW is secreted onto the surface of skin 1 by stress, it is difficult to measure skin-electrode contact resistance Rct due to the sweat SW secreted by the following stress. Accordingly, even if the sensor for measuring skin conductivity is continuously attached to skin 1, the sweat SW can be discharged into the air through the through holes 140 formed at the sensor for measuring skin conductivity. Thus, it is possible to continuously and accurately measure a user's stress levels.

In the sensor for measuring skin conductivity according to the embodiment of the present invention, the uneven structure 130 is provided on the electrode 120 provided on the base board 110 made of the flexible material to come into close contact with skin 1, whereby it is possible to measure that skin-electrode contact resistance Rct is drastically reduced as a electrical contact surface CS area between skin 1 and the electrode 120 is enlarged by the sweat SW secreted onto the surface of skin 1. Thus, electrodermal activity can be efficiently measured.

In addition, the electrode 120 includes the first electrode 121 and the second electrode 122, the uneven structure 130 is provided on the first electrode 121 and the second electrode 122, and also on the base board 110 at the locations between the first and second electrodes 121 and 122, whereby the electrical signal passing between the first and second electrodes 121 and 122 can be transmitted through not only the inside of skin 1 but also through the sweat SW and the uneven structure 130. Thus, electrodermal activity can be efficiently measured.

Moreover, the plurality of through holes 140 is formed through the base board 110, the electrode 120, and the uneven structure 130 in the direction perpendicular to the surface of the base board 110, whereby the sweat SW secreted onto the surface of skin 1 can be rapidly evaporated by air flowing through the through holes 140. Thus, in measuring skin electrical activity, it is possible to eliminate measurement errors that occur when the sweat SW is accumulated on the uneven structure 130.

Hereinafter, a method of manufacturing a sensor for measuring skin conductivity according to an embodiment of the present invention will be described with reference to the accompanying drawings.

Figure 13A:
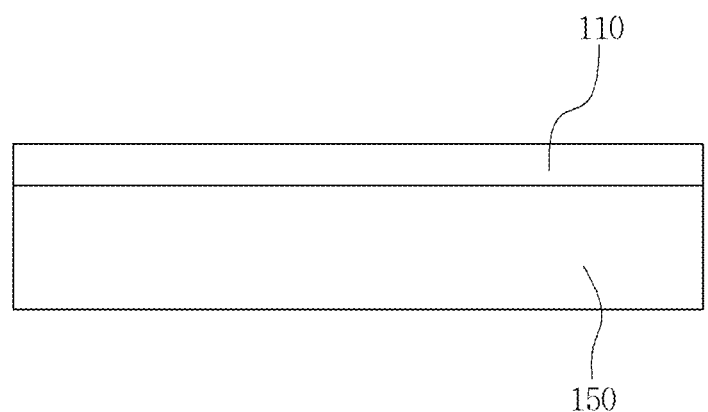
FIGS. 13A, 13B, and 13C are cross-sectional views showing a step of forming the electrode in a method of manufacturing the sensor for measuring skin conductivity according to an embodiment of the present invention.
Figure 13B:
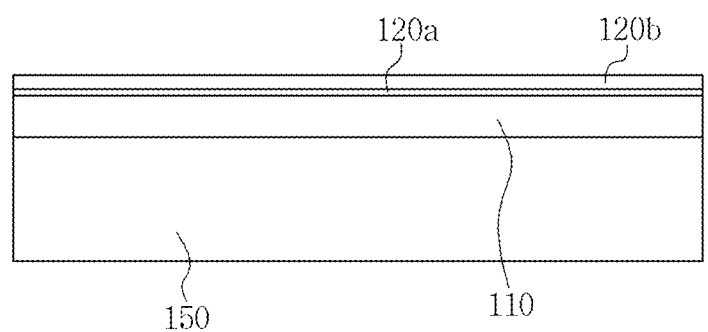
Figure 13C:
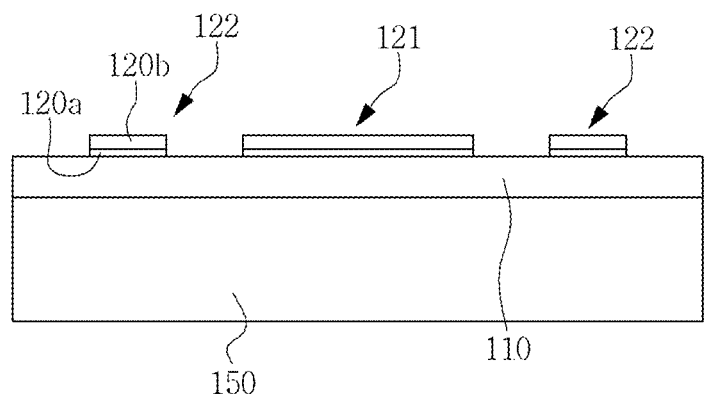
Figure 14A:
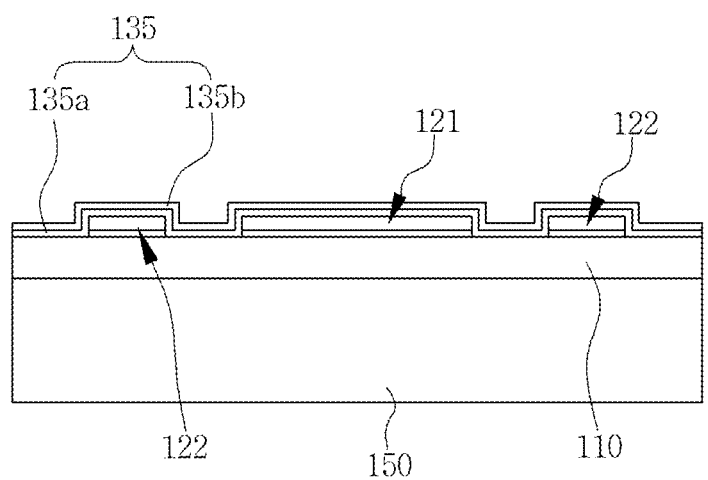
FIGS. 14A, 14B, and 14C are cross-sectional views showing a step of forming the uneven structure in the method of manufacturing the sensor for measuring skin conductivity according to the embodiment of the present invention.
Figure 14B:
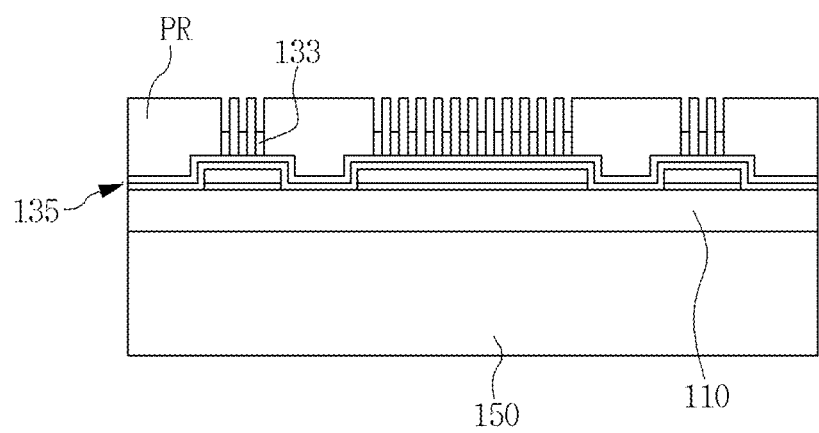
Figure 14C:
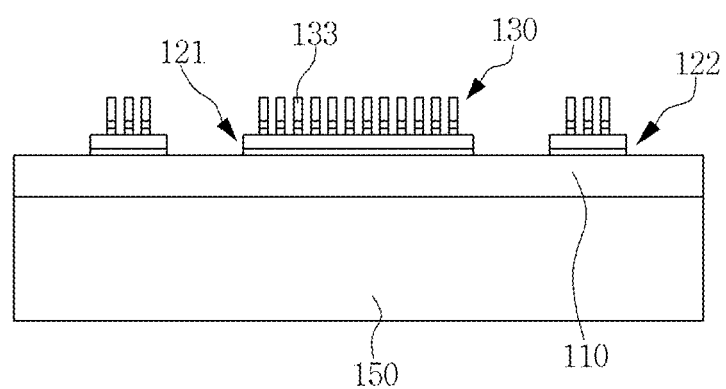
Figure 15:
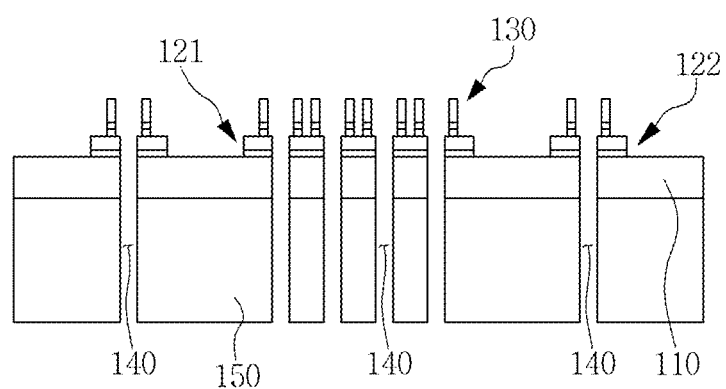
FIG. 15 is a cross-sectional view showing a step of forming a through hole in the method of manufacturing the sensor for measuring skin conductivity according to the embodiment of the present invention.

FIGS. 13A, 13B, and 13C are cross-sectional views showing a step of forming the electrode 120 in the method of manufacturing the sensor for measuring skin conductivity according to an embodiment of the present invention, FIGS. 14A, 14B, and 14C are cross-sectional views showing a step of forming the uneven structure 130 in the method of manufacturing the sensor for measuring skin conductivity according to the embodiment of the present invention, and FIG. 15 is a cross-sectional view showing a step of forming a through hole 140 in the method of manufacturing the sensor for measuring skin conductivity according to the embodiment of the present invention. FIGS. 13A to 15 are cross-sectional views taken along line A-A' of FIG. 4.

The method of manufacturing the sensor for measuring skin conductivity according to the embodiment of the present invention includes preparing the base board 110 on a carrier board 150, forming the electrode 120 on the base board 110 by forming and patterning a conductive material, forming the uneven structure 130 on the electrode 120 such that the electrical contact surface CS area with skin 1 is enlarged by the sweat SW secreted onto the surface of skin 1, and removing the carrier board 150.

As shown in FIG. 13A, first, the base board 110 is placed on the carrier board 150. The carrier board 150 serves to support the base board 110 in a manufacturing process.

Next, as shown in FIG. 13B, the conductive material is formed to form the electrode 120 on the base board 110. For example, the conductive material may be a metal layer, wherein a Ti layer 120a may be formed on the base board 110 to a thickness of about 300 Å, and an Au layer 120b may be formed on the Ti layer 120a to a thickness of about 1000 Å.

Next, as shown in FIG. 13C, the electrode 120 is patterned using a semiconductor manufacturing process such as a photoresist PR and etching. At this time, the electrode 120 may be formed as shown in FIGS. 8A, 8B, and 8C.

Next, as shown in FIG. 14A, a seed layer 135 is further formed on the base board 110 and the electrode 120. The seed layer 135 is formed prior to forming the uneven structure 130 on the electrode 120 or the base board 110, thereby efficiently forming the uneven structure 130 on the electrode 120 or the base board 110. For example, in the seed layer 135, a Ti layer 135a may be formed to a thickness of about 300 Å on the base board 110, and an Au layer 135b may be formed on the Ti layer 135a to a thickness of about 500 Å.

Next, as shown in FIG. 14B, the photoresist PR is formed on the seed layer 135, and a portion where the protrusions 133 will be formed is patterned. The photoresist PR may be patterned to form the protrusions 133 only on the electrode 120, or may be patterned to form the protrusions 133 on both the electrode 120 and the base board 110. Then, the uneven structure 130 is formed on the electrode 120 or the base board 110 by using the patterned photoresist PR as a mask and by plating or vapor-depositing a metal such as Au.

Next, as shown in FIG. 14C, the photoresist PR is removed, the seed layer 135 on which no protrusions 133 are formed is removed, and the carrier board 150 is removed, thereby manufacturing a sensor for measuring skin conductivity.

Next, after the forming of the uneven structure 130, the method may further include forming a plurality of through holes 140 passing through the base board 110, the electrode 120, and the uneven structure 130 in the direction perpendicular to the surface of the base board 110. Since the forming of the through holes 140 is carried out after the electrode 120 and the uneven structure 130 are formed on the base board 110, the through holes 140 can be easily formed.

Although a preferred embodiment of the present invention has been described for illustrative purposes, those skilled in the art will appreciate that various modifications, additions and substitutions are possible, without departing from the scope and spirit of the invention as disclosed in the accompanying claims.

Further, simple changes and modifications of the present invention are appreciated as included in the scope and spirit of the invention, and the protection scope of the present invention will be defined by the accompanying claims.

What is claimed is:

1. A sensor for measuring skin conductivity, the sensor comprising:
    a flexible base board comprising a non-conductive surface;
    a first conductive pattern provided over the non-conductive surface of the flexible base board, and configured to apply, a first electrical signal, to skin, received from an external circuit that is electrically insulated from the non-conductive surface;
    a first set of conductive protrusions formed over and in direct physical contact with the first conductive pattern, wherein the first set of conductive protrusions are configured to contact the skin for providing electronic connection between the skin and the first conductive pattern and to increase an electrical contact area with the skin when sweat permeates between at least some of the first set of conductive protrusions;
    a second conductive pattern provided over the non-conductive surface of the flexible base board, electrically insulated from the first conductive pattern by the flexible base board, and configured to receive a second electrical signal caused by the first electrical signal from the skin and to transmit the second electrical signal to the external circuit;
    a second set of conductive protrusions formed over and in direct physical contact with the second conductive pattern and spaced apart from the first set of conductive protrusions by a gap, wherein the second set of conductive protrusions are configured to contact the skin for elecrical connection between the skin and the second conductive pattern and to increase an electrical contact area with the skin when the sweat permeates between at least some of the second set of conductive protrusions; and
    a third set of conductive protrusions formed over and in direct physical contact with the non-conductive surface of the flexible base board and located in the gap between the first second sets of conductive protrusions, wherein the third set of conductive protrusions are electrically insulated from the external circuit and the first and second sets of conductive patterns by the flexible base board such that when no sweat permeates between at least some of the third set of conductive protrusions, the third set of conductive protrusions do not provide a path for an electrical signal to flow between the first and second sets of conductive protrusions, and
    wherein upper ends of the third set of conductive protrusions are aligned with upper ends of the first set of conductive protrusions and upper ends of the second set of conductive protrusions in a direction parallel to the non-conductive surface of the flexible base board such that when the sweat permeates between at least some of the third set of conductive protrusions, the third set of conductive protrusions and the sweat in combination provide a path for an electrical signal to flow between the first and second sets of conductive protrusions along an external surface of the skin.

2. The sensor of claim 1, wherein the first set of conductive protrusions include gaps defined therebetween so that sweat secreted onto the external surface of skin permeates between the gaps.

3. The sensor of claim 2, further comprising:
    at least one through hole formed through the flexible base board and the first conductive pattern, the at least one through hole configured to evaporate sweat therethrough.

4. The sensor of claim 1, wherein each of the first conductive pattern and the second conductive pattern includes a plurality of branches such that the branches of the first conductive pattern and the branches of the second conductive pattern are arranged in a comb pattern.

5. The sensor of claim 1, wherein the second conductive pattern substantially surrounds the first conductive pattern such that when viewed in a cross section, the first conductive pattern is located between a first portion of the second conductive pattern and a second portion of the second conductive pattern.

6. The sensor of claim 1, wherein a plurality of through holes are formed to pass through the flexible base board, the plurality of through holes configured to evaporate sweat permeating between the external surface of the skin and the first to third sets of conductive protrusions.

7. The sensor of claim 6, wherein the plurality of through holes are formed to be perpendicular to the non-conductive surface of the flexible base board.

* * * * *